(12) United States Patent
Sidransky

(10) Patent No.: US 6,291,163 B1
(45) Date of Patent: *Sep. 18, 2001

(54) METHOD FOR DETECTING CELL PROLIFERATIVE DISORDERS

(75) Inventor: David Sidransky, Baltimore, MD (US)

(73) Assignee: The Johns Hopkins University School of Medicine, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/968,733

(22) Filed: Aug. 28, 1997

Related U.S. Application Data

(60) Provisional application No. 60/025,805, filed on Aug. 28, 1996.

(51) Int. Cl.[7] .............................. C12Q 1/68; C12P 19/34; C07H 21/04

(52) U.S. Cl. .......................... 435/6; 435/91.2; 536/24.31; 536/24.33

(58) Field of Search .................. 435/6, 91.2; 536/24.33, 536/24.31

(56) References Cited

U.S. PATENT DOCUMENTS

| | | | |
|---|---|---|---|
| 4,800,159 | 1/1989 | Mullis et al. | 435/172.3 |
| 5,075,217 | 12/1991 | Weber | 435/6 |
| 5,380,645 | 1/1995 | Vogelstein | 435/6 |
| 5,468,610 | * 11/1995 | Polymeropoulos et al. | 435/6 |
| 5,492,808 | 2/1996 | De La Chapelle et al. | 435/6 |
| 5,541,067 | 7/1996 | Perlin | 435/6 |
| 5,578,450 | 11/1996 | Thibodeau et al. | 435/6 |
| 5,952,170 | * 9/1999 | Stroun et al. | 435/6 |

FOREIGN PATENT DOCUMENTS

| | | |
|---|---|---|
| 229166A | * 9/1996 | (GB) . |
| WO 94/19492 | 9/1994 | (WO) . |
| WO94/19492 | 9/1994 | (WO) . |
| 95/16792 | * 6/1995 | (WO) . |

OTHER PUBLICATIONS

Hiroshige, K. Nippon Jibiinkoka Gakkai Kaiho. Aug. 2000. 103(8): 928–36.*

Matsubara et al. Intervirology. 2000. 43(1): 16–19.*

Miozzo et al. Cancer Research. 56; 2285–2288, May 1996.*

Mao et al. Proceedings of the National Academy of Sciences. 91: 9871–9875, May 1996.*

Mao et al. Scienc. 271:659–662, Feb. 1996.*

Gerkin et al., "Genetic and Physical Mapping of Simple Sequence Repeat Containing Sequence Tagged Sites from the Human Genome", Database GenBank, Accession No. L16332 (1993).

Murray et al., "Cooperative Himan Linkage Center", Database GenBank, Accession No. G029239 (1993).

Sidransky et al., "Identification of p53 Gene Mutations in Bladder Cancers and Urine Samples," *Science*, vol. 252, pp. 706–709, May 3, 1991.

Noble, et al., "A Rapid PCR–Based Method to Distinguish Between Fetal and Maternal Cells in Chorionic Biopsies Using Microsatellite Polymorphism," *Disease Markers*, vol. 9, pp. 301–306, 1991.

Sidransky, et al., "Identification of ras Oncogene Mutations in the Stool of Patients with Curable Colorectal Tumors," *Science*, vol. 256, pp. 102–105, Apr. 3, 1992.

Peltomaki, et al., "Genetic Mapping of a Locus Predisposing to Human Colorectal Cancer," *Science*, vol. 260, pp. 810–812, May 7, 1993.

Aaltonen, L., et al., "Clues to the Pathogenesis of Familial Colorectal Cancer," *Science* vol. 260, pp. 812–816, May 7, 1993.

Thibodeau, S., et al., "Microsatellite Instability in Cancer of the Proximal Colon," *Science*, vol . 260, pp. 816–819, May 7, 1993.

Ionov, et al., "Ubiquitous somatic mutations in simple repeated sequences reveal a new mechanism for colonic carcinogenesis," *Nature*, vol. 363, pp. 558–561, Jun. 10,1993.

Strand, et al., "Destabilization of tracts of simple repetitive DNA in yeast by mutations affecting DNA mismatch repair," *Nature*, vol. 365, pp. 274–276, Sep. 16, 1993.

Peltomaki, et al, "Microsatellite Instability is Associated with Tumors That Characterize the Hereditary Non–Polyposis Colorectal Carcinoma Syndrome," *Cancer Research*. vol. 53, pp. 5853–5855, Dec. 15, 1993.

Palombo, et al., "Mismatch repair and cancer", *Nature*, vol. 367, p. 417, Feb. 3, 1994.

(List continued on next page.)

*Primary Examiner*—Carla J. Myers
(74) *Attorney, Agent, or Firm*—Banner & Witcoff, Ltd.

(57) ABSTRACT

The present invention relates to the detection of a cell proliferative disorder associated with alterations of microsatellite DNA in a sample. The microsatellite DNA can be contained within any of a variety of samples, such as urine, sputum, bile, stool, cervical tissue, saliva, tears, or cerebral spinal fluid. The invention is a method to detect an allelic imbalance by assaying microsatellite DNA. Allelic imbalance is detected by observing an abnormality in an allele, such as an increase or decrease in microsatellite DNA which is at or corresponds to an allele. An increase can be detected as the appearance of a new allele. In practicing the invention, DNA amplification methods, particularly polymerase chain reactions, are useful for amplifying the DNA. DNA analysis methods can be used to detect such a decrease or increase. The invention is also a method to detect genetic instability of microsatellite DNA. Genetic instability is detected by observing an amplification or deletion of the small, tandem repeat DNA sequences in the microsatellite DNA which is at or corresponds to an allele. The invention is also a kit for practicing these methods.

17 Claims, 5 Drawing Sheets

OTHER PUBLICATIONS

Wang, et al., "Brief Report: Polymorphic Microsatellite Markers for the Diagnosis of Graft–Versus–Host Disease," *The New England Journal of Medicine*, vol. 330, No. 6, pp. 398–401, Feb. 10, 1994.

King, et al., "A Polymerase Chain Reaction–Based Microsatellite Typing Assay Used for Tumor Cell Line Identification," *American Journal of Pathology*, vol. 144, No. 3, pp. 486–491, Mar. 1994.

Hayashi, et al., "Genetic Diagnosis Identifies Occult Lymph Node Metastases Undetectable by the Histopathological Method," *Cancer Research*, vol. 54, pp. 3853–3856, Jul. 15, 1994.

Homaira Nawroz et al. "Microsatellite alterations in scrum DNA of head and neck cancer patients" Nature Medicine, vol. 2, No. 9, Sep. 1996.

Li Mao et al. "Molecular Detection of Primary Bladder Cancer by Microsatellite Analysis" Science, vol. 271, Feb. 2, 1996.

* cited by examiner

FIG. 1

Characteristics of patients with bladder lesions. Cyto, cytology; Alt, microsatellite alteration (expansion or deletion); ND, not done; NA, not applicable; transitional cell carcinoma; AC, adenocarcinoma; mucin, mucinous; inflamm, inflammation. Grades and stages were assigned following the recommendations of the American Joint Committee on Cancer after examination by pathology (20). Control patients presented without signs or symptoms of bladder cancer (for example, benign prostatic enlargment). Four of the five control patients underwent cystoscopy and were free of any suspicious lesions.

| Patient | Age/Sex | Tumor grade | Pathology | Stage | Urine analysis | | |
|---|---|---|---|---|---|---|---|
| | | | | | Cyto | LOH | Alt |
| 1 | 80/F | G3 | TCC | T3N0M0 | + | + | - |
| 2 | 43/M | ND | TCC | | ND | + | - |
| 3 | 75/M | G3 | TCC | T1N0M0 | - | - | + |
| 4 | 60/M | G1 | TCC in situ | TaN0M0 | - | + | - |
| 5 | 78/F | G2 | TCC | | + | + | + |
| 6 | 45/M | G1 | TCC | T1N0M0 | Atypia | - | + |
| 7 | 72/M | * | AC + mucin | | + | + | - |
| 8 | 84/M | ND | TCC | T1N0M0 | + | + | + |
| 9 | 75/M | G3 | TCC | T1N0M0 | + | - | - |
| 10 | 82/F | G3 | TCC | T4N2M0 | Atypia | + | - |
| 11 | 80/M | G3 | TCC in situ | TaN0M0 | Atypia | + | + |
| 12 | 67/M | G2 | TCC | T1N0M0 | ND | + | - |
| 13 | 75/M | G3 | TCC | T2N0M0 | - | + | + |
| 14 | 86/F | G3 | TCC in situ | TaN0M0 | - | + | - |
| 15 | 71/M | G2 | TCC | | - | + | - |
| 16 | 54/M | G3 | TCC | T3N0M0 | + | + | + |
| 17 | 51/M | G2 | TCC | T1N0M0 | + | + | - |
| 18 | 72/M | * | Intraductal TCC | | + | + | + |
| 19 | 65/M | G2 | TCC | T2N0M0 | + | + | - |
| 20 | 55/F | G1-G2 | TCC | TaN0M0 | - | - | + |
| 21 | 65/F | NA | Atypia/inflamm | | ND | + | + |
| 22 | 86/M | NA | Chronic inflamm | | ND | - | - |
| 23 | 71/M | NA | Chronic inflamm | | - | - | - |
| 24 | 79/M | NA | Atypia/inflamm | | Atypia | + | - |
| 25 | 65/M | NA | Normal | | - | - | - |
| 26 | 70/M | Control patient without cancer | | NA | ND | - | - |
| 27 | 70/M | Control patient without cancer | | NA | ND | - | - |
| 28 | 54/M | Control patient without cancer | | NA | ND | - | - |
| 29 | 35/M | Control patient without cancer | | NA | ND | - | - |
| 30 | 68/M | Control patient without cancer | | NA | ND | - | - |

* Prostatic iossa.

FIG. 2 Microsatellight analysis of urine sediment. T, tumor (in patients 22 and 23, nonneoplastic tissue); U, urine; L, LOH; S, allele shift (alteration); •, tumor or biopsy not available. Cytology symbols: N, normal; +, positive for tumor; -, negative for tumor; A, atypia; ND, not done. The chromosomal location of each marker follows the letter D (for example, D16S310, chromosome 16). Additionally, gene loci are ACTBP2 on chromosome 6, FGA on 4, MBP on 18, MJD on 14, and IFNA on 9.

Of 25 total patients with clinical suspicion of cancer, 20 had a confirmed diagnosis of cancer by pathology. Of the 20, 19 (95%) had identical clonal alterations in their tumor and urine samples, and at least 9 (45%) were cytologically negative for cancer (2 ND). The five control patients (no shown) had no molecular changes in urine. LOH was observed consistently in urine but was obscured in tumors (for example, patient 17) because only a few neoplastic cells were present in the tumor biopsy or because infiltration with normal lymphocytes occured.

| Patient | Cytology | Molecular changes at marker |||||||||||||||||||||||||
|---|---|---|---|---|---|---|---|---|---|---|---|---|---|---|---|---|---|---|---|---|---|---|---|---|---|
| | | ACTBP2 || D16S310 || FGA || D21S1245 || D4S243 || D16S476 || D9S747 || D18S51 || MBP || MJD || D9S162 || IFNA || D9S171 ||
| | | T | U | T | U | T | U | T | U | T | U | T | U | T | U | T | U | T | U | T | U | T | U | T | U |
| 1 | + | • | L | | | | | | | | | | L | | | | | | | | | | | | L |
| 2 | ND | | | | | | | | | | • L | | L | | | | | | | | | | | | L |
| 3 | - | | | | | | | | | | | | | | | | | | | | | | | | |
| 4 | - | L L | | | L L | | | | | | | | | | L L | | | | | | | | | | L |
| 5 | + | L L | | L L | | | | S S | | | | S | | | | | | | | | | | | | |
| 6 | A | L L S | | | | | | | | | L | | | | | | L L | | • S | | | | | | L |
| 7 | + | | | | | | | | | | | • S L L | | | | L L | | | | | | | | | L |
| 8 | + | | | | | | | | | | | | | | | | | | | | | | | L L | |
| 9 | A | | | | | | | | L • | | | | | | L L | | L | | | | | | | | L |
| 10 | A | | | | | | | • S | | | | | | | | | | | | • S | | L L | | • | L |
| 11 | ND | | | | | | | • | | L | | | | • L | | | | | | | | | | | |
| 12 | - | | | | | | | | L L | | | | L L | | | | | | | | | | | | |
| 13 | N | L L | | | | | | S S | | | | | | L L | | L L | | | | L L | | | | | |
| 14 | N | L L | | | | | | S S | | | | | | | | | | | | | | L L | | | |
| 15 | + | L L | | | | L L | | • L | | | | | | L L | | | | | | | | | | | L |
| 16 | + | | | | | S S | | | | | | | | | | | | | | | | | | | |
| 17 | + | | | | | | | | | S S | | | | | | | | | | | | | | | |
| 18 | + | | | • S | | | | | | | | | | | | | | | | | | | | | |
| 19 | - | | | | | | | | | | | | | | | | | | | | | | | | |
| 20 | ND | | | | | | | | | | | | | | | | | | | | | | | | |
| 21 | ND | | | | | | | | | | | | | | | | | | | | | | | | |
| 22 | - | | | | | | | • L | | | | | | | | | | | | | | | • L | • | L |
| 23 | A | | | | | | | | | | | | | | | | | | | | | | | | |
| 24 | - | | | | | | | | | | | | | | | | | | | | | | | | |

FIG. 3

| | | | Tumor | | Serum | | | Clinical |
|---|---|---|---|---|---|---|---|---|
| ID# | Age/sex | Stage | LOH/shift | | LOH/shift | | O/S | outcome |
| H1 | 84/M | $T_3N_1M_0$ | + | + | - | + | 10 | DOD |
| H2 | 80/M | $T_4N_0M_0$ | + | - | + | - | 12 | DOD |
| H3 | 51/M | $T_3N_2M_0$ | + | + | + | + | 36 | NED |
| H4 | 50/M | $T_4N_{2b}M_0$ | + | - | + | - | 44 | AWD, distant mets |
| H5 | 63/M | $T_3N_1M_0$ | + | + | + | + | 20 | DOD, distant mets |
| H6 | 59/F | $T_3N_1M_0$ | + | - | + | - | 04 | DOD, distant mets |
| H7 | 46/M | $T_2N_{2a}M_0$ | + | - | - | - | 14 | NED |
| H8 | 85/F | $T_4N_0M_0$ | + | - | - | - | 34 | NED |
| H9 | 62/M | $T_3N_3M_0$ | - | - | - | - | 32 | NED |
| H10 | 72/F | $T_3N_0M_0$ | + | - | - | - | 12 | NED |
| H11 | 41/M | $T_2N_{2b}M_0$ | + | - | - | - | 36 | NED |
| H12 | 56/M | $T_3N_{2c}M_0$ | + | - | - | - | 29 | NED |
| H13 | 45/M | $T_3N_{2b}M_0$ | + | - | - | - | 05 | DOD |
| H14 | 91/M | $T_3N_{2b}M_0$ | - | - | - | - | 0 | LTF |
| H15 | 64/M | aud. canal | + | - | - | - | 10 | DOD |
| H16 | 66/M | $T_1N_0M_0$ | + | - | - | - | 30 | NED |
| H17 | 46/M | $T_2N_0M_0$ | + | + | - | - | 36 | NED |
| H18 | 49/M | $T_1N_0M_0$ | + | - | - | - | 36 | NED |
| H19 | 40/M | $T_1N_0M_0$ | + | + | - | - | 56 | NED |
| H20 | 61/F | $T_1N_0M_0$ | - | - | - | - | 88 | DOD |
| H21 | 76/M | $T_2N_0M_0$ | + | - | - | - | 44 | NED |

Clinical data and results of microsatellite analysis. Column 2 shows corresponding age at the time of diagnosis and sex. Stage of HNSCC, according to the tumor-node-metastasis (TNM) staging system of the American Joint Committee on Cancer[20], is listed in column 3. Microsatellite data of tumor and plasma DNA are indicated by + for presence of LOH or shift and - for absence of these findings. O/S states the overall survival (survival regardless of disease status) period in months for each patient. Clinical outcome abbreviations: DOD, died of disease; AWD, alive with disease; NED, no evidence of disease; mets, metastases; and LTF, lost to follow-up.

FIG. 4

Detailed microsatellite analysis of patients with alterations in plasma

| Patient | IFNA | D9S200 | D9S161 | D9S156 | D3S1284 | D3S1238 | D14S50 | D21S1245 | CHRNB1 | D17S786 | FGA | DRPLA |
|---|---|---|---|---|---|---|---|---|---|---|---|---|
| H1 T | LOH | Ret | Ret | | | | Ret | Shift | | | Ret | |
| S | Ret | Ret | Ret | | | | Ret | Shift | | | Ret | |
| H2 T | | LOH | | | | LOH | LOH | | Ret | | Ret | |
| S | | LOH | | | | LOH | LOH | | Ret | | Ret | |
| H3 T | | Ret | LOH | | Ret | Ret | | LOH | Shift | | | Ret |
| S | | Ret | LOH | | Ret | Ret | | LOH | Shift | | | Ret |
| H4 T | | LOH | Ret | Ret | Ret | LOH | | LOH | | Ret | Ret | Ret |
| S | | Ret | Ret | Ret | Ret | LOH | | LOH | | Ret | Ret | Ret |
| H5 T | | LOH | LOH | LOH | LOH | Ret | | Shift | Ret | | Ret | Ret |
| S | | LOH | LOH | LOH | LOH | Ret | | Shift | Ret | | Ret | Ret |
| H6 T | Ret | | | Ret | Ret | LOH | Ret | Ret | Ret | | Ret | LOH |
| S | Ret | | | Ret | Ret | LOH | Ret | Ret | Ret | | Ret | LOH |

Summary of six patients with LOH (loss of heterozygosity) or shifts (new alleles) demonstrated after microsatellite analysis of serum (S) DNA with comparison to analysis in tumor (T). All samples were compared to constitutive normal DNA from lymphocytes (see text). Empty boxes represent noninformative markers and Ret (retention) indicates informative markers without evidence of loss.

FIG. 5

Summary of genetic changes, primary and follow-up data and cytology in study patients

| Patient | Primary molecular status | Primary clinical status | Molecular FU status | First molecular detection | Clinical FU status | Cytology | Tumor recurrence | Final follow-up |
|---|---|---|---|---|---|---|---|---|
| B565 | + | pT1, G3 | negative | | NED | negative | | 26 months |
| B566 | + | pTa, G1 | negative | | NED | negative | | 26 months |
| B580 | + | pT2, G3 | + | 6 months | pT2, G3† | negative | 6 months | 26 months |
| B603 | negative | pTa, G1 | + | 9 months | pTa, G1 | negative | 13 months | 25 months |
| B604 | + | pT3b, G3 | negative | | NED | negative | | 25 months |
| B608 | negative | pTa, G1 | negative | | NED | negative | | 12 months |
| B687 | + | pT3b, G3 | + | 4 months | PT3b, G3 | ND | 4 months | 13 months |
| B694 | + | pTa, G1-2 | + | 11 months | pTa, G1-2 | negative | 11 months | 17 months |
| B695 | + | pT4a, G3 | + | 14 months | pT4a, G3† | ND | 14 months | 21 months |
| B701 | + | pT3, G2 | negative | | NED | negative | | 6 months |
| B704 | + | pT4a, G3 | negative | | NED | negative | | 20 months |
| B716 | * | pTa, G2 | + | 5 months | pTa, G2 | negative | 5 months | 18 months |
| B799 | + | pT1, G3 | negative | | NED | ND | | 12 months |
| B806 | + | pTa, G1-2 | negative | | NED | negative | | 13 months |
| B816 | + | pTa, G1 | + | 6 months | pTa, G1 | positive | 6 months | 9 months |
| B874 | + | pTa, G2-3 | negative | | pTa, G1 | negative | 5 months | 11 months |
| B884 | + | pTa, G1 | negative | | NED | negative | | 8 months |
| B899 | + | pT3a, G2 | negative | | NED | negative | | 10 months |
| B903 | + | pTa, G2 | + | 4 months | pTa, G1-2 | negative | 4 months | 8 months |
| B918 | + | pT3b, G2 | + | 4 months | ‡ | ND | 9 months | 10 months |
| B919 | + | pTa, G2 | + | 4 months | pTa, G2 | negative | 4 months | 10 months |

In the second column, the molecular status of urinalysis (+, positive) is listed followed by the stage and grade of the primary lesion in the next column. The next column shows the presence of a positive molecular test any time during follow-up, and the time of first detection during the study is listed in the following column. The next column provides the most recent clinical status obtained by cystoscopy (and biopsy if indicated) and indicates the stage and grade of recurrent lesions[15]. The next-to-last column provides the time of actual tumor recurrence; note that in patients B603 and B918, disease recurrence was detected by molecular analysis several months before actual identification of the tumor by clinical studies. Patient B874 was the only patient with recurrence not detected by the molecular test. In the final column, total follow-up time for each patient is listed.
Abbreviations: FU, follow-up; ND, not done; NED, no evidence of disease.
*Initial urine not available.
†Persistant disease after partial cystectomy.
‡Vaginal recurrance after radical cystectomy.

SEQUENCE LISTING (1) GENERAL INFORMATION:

(iii) NUMBER OF SEQUENCES: 64

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:1:

CTTGTGTCCC GGCGTCTG                                                18

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:2:

CAGCCCAGCA GGACCAGTA                                               19

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

TGGTAACAGT GGAATACTGA C                                            21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

ACTGATGCAA AAATCCTCAA C                                            21

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

```
GATGGGCAAA CTGCAGGCCT GGGAAG                                               26

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

GCTACAAGGA CCCTTCGAGC CCCGTTC                                              27

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

GATGGTGATG TGTTGAGACT GGTG                                                 24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:8:

GAGCATTTCC CCACCCACTG GAGG                                                 24

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

GTTCTGGATC ACTTCGCGGA                                                      20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:10:

TGAGGATGGT TCTCCCCAAG                                                      20
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

AGTGGTGAAT TAGGGGTGTT                                                        20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

CTGCCATCTT GTGGAATCAT                                                        20

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

CTGTGAGTTC AAAACCTATG G                                                    21

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:14:

GTGTCAGAGG ATCTGAGAAG                                                        20

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:15:

GCACGCTCTG GAACAGATTC TGGA                                              24

(2) INFORMATION FOR SEQ ID NO:16:

(i) SEQUENCE CHARACTERISTICS:
        (A) LENGTH: 24 base pairs (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:16:

ATGAGGAACA GCAACCTTCA CAGC                                          24

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:17:

TCACTCTTGT CGCCCAGATT                                               20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:18:

TATAGCGGTA GGGGAGATGT                                               20

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:19:

TGCAAGGAGA AAGAGAGACT GA                                            22

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:20:

AACAGGACCA CAGGCTCCTA                                              20

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:21:

TCTCTTTCTT TCCTTGACAG GGTC                                              24

(2) INFORMATION FOR SEQ ID NO:22:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:22:

CAGTGTGGTC CCAAATTTGA AATGG                                             25

(2) INFORMATION FOR SEQ ID NO:23:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:23:

GTGCTGACTA GGGCAGCTT                                                    19

(2) INFORMATION FOR SEQ ID NO:24:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:24:

TGTGACCTGC ACTCGGAAGC                                                   20

(2) INFORMATION FOR SEQ ID NO:25:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:25:

CCTTTCCTTC CTTCCTTCC                                                    19

(2) INFORMATION FOR SEQ ID NO:26:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:26:

```
CACAGTCAGG TCAGGCTATC AG                                                    22

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:27:

TTTTTGAGAT AGAGTCTCAC TGTG                                                  24

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:28:

CCACAGTCTA AGCCAGTCTG A                                                     21

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:29:

GAATTTTGCT CTTGTTGCCC AG                                                    22

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:30:

AGACTGAAGT CAATGAACAA CAAC                                                  24

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:31:

GGCTGTGAAC ATGGCCTAGG TC                                                    22

(2) INFORMATION FOR SEQ ID NO:32:
```

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO:32:

TTGGGGTGGT GCCAATGGAT GTC                                                23

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:33:

CAGACGCCGG GACACAAG                                                      18

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:34:

TACTGGTCCT GCTGGGCTG                                                     19

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:35:

GTCAGTATTA CCCTGTTACC A                                                  21

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:36:

GTTGAGGATT TTTGCATCAG T                                                  21

(2) INFORMATION FOR SEQ ID NO:37:

(i) SEQUENCE CHARACTERISTICS:
        (A) LENGTH: 26 base pairs
        (B) TYPE: nucleic acid (C) STRANDEDNESS: single
        (D) TOPOLOGY: linear (ii) MOLECULE TYPE: oligonucleotide (xi) SEQUENCE DESCRIPTION: SEQ ID NO:37:

CTTCCCAGGC CTGCAGTTTG CCCATC                                        26

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:38:

GAACGGGGCT CGAAGGGTCC TTGTAGC                                       27

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:39:

CACCAGTCTC AACACATCAC CATC                                          24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:40:

CCTCCAGTGG GTGGGAAAT GCTC                                           24

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:41:

TCCGCGAAGT GATCCAGAAC                                               20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:42:

CTTGGGGAGA ACCATCCTCA                    20

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:43:

AACACCCCTA ATTCACCACT                    20

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:44:

ATGATTCCAC AAGATGGCAG                    20

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:45:

CCATAGGTTT TGAACTCACA G                  21

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:46:

CTTCTCAGAT CCTCTGACAC                    20

(2) INFORMATION FOR SEQ ID NO:47:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:47:

TCCAGAATCT GTTCCAGAGC GTGC               24

(2) INFORMATION FOR SEQ ID NO:48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:48:

```
GCTGTGAAGG TTGCTGTTCC TCAT                                    24
```

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:49:

```
AATCTGGGCG ACAAGAGTGA                                         20
```

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:50:

```
ACATCTCCCC TACCGCTATA                                         20
```

(2) INFORMATION FOR SEQ ID NO:51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:51:

```
TCAGTCTCTC TTTCTCCTTG CA                                      22
```

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:52:

```
TAGGAGCCTG TGGTCCTGTT                                         20
```

(2) INFORMATION FOR SEQ ID NO:53:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: oligonucleotide (xi) SEQUENCE DESCRIPTION: SEQ ID NO:53:

GACCCTGTCA AGGAAAGAAA GAGA                                          24

(2) INFORMATION FOR SEQ ID NO:54:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:54:

CCATTTCAAA TTTGGGACCA CACTG                                         25

(2) INFORMATION FOR SEQ ID NO:55:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:55:

AAGCTGCCCT AGTCAGCAC                                                19

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:56:

GCTTCCGAGT GCAGGTCACA                                               20

(2) INFORMATION FOR SEQ ID NO:57:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:57:

GGAAGGAAGG AAGGAAAGG                                                19

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: oligonucleotide (xi) SEQUENCE DESCRIPTION: SEQ ID NO:58:

CTGATAGCCT GACCTGACTG TG                                                    22

(2) INFORMATION FOR SEQ ID NO:59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:59:

CACAGTGAGA CTCTATCTCA AAAA                                                  24

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:60:

TCAGACTGGC TTAGACTGTG G                                                     21

(2) INFORMATION FOR SEQ ID NO:61:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:61:

CTGGGCAACA AGAGCAAAAT TC                                                    22

(2) INFORMATION FOR SEQ ID NO:62:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:62:

GTTGTTGTTC ATTGACTTCA GTCT                                                  24

(2) INFORMATION FOR SEQ ID NO:63:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide -continued

```
    (xi) SEQUENCE DESCRIPTION: SEQ ID NO:63:

GACCTAGGCC ATGTTCACAG CC                                              22

(2) INFORMATION FOR SEQ ID NO:64:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: oligonucleotide (xi) SEQUENCE DESCRIPTION: SEQ ID NO:64:

GACATCCATT GGCACCACCC CAA                                             23
```

METHOD FOR DETECTING CELL PROLIFERATIVE DISORDERS

CROSS REFERENCE TO RELATED APPLICATIONS

The present invention claims priority under 35 U.S.C. §119(e) from Provisional Application Serial No. 60/025,805, filed Aug. 28, 1996.

BACKGROUND OF THE INVENTION

1. Field of the Invention

The present invention relates generally to the detection of a target nucleic acid sequence and specifically to the detection of microsatellite DNA sequence mutations associated with a cell proliferative disorder.

2. Description of Related Art

Cancer remains a major cause of mortality worldwide. Despite advancements in diagnosis and treatment, the overall survival rate has not imrved significantly in the past twenty years. There remains an unfulfilled need for a more sensitive means of early diagnosis of tumors, before the cancer progresses.

One of the most serious cancers is bladder cancer. Bladder cancer is the fourth most common cancer in men and the eighth most common in women. Transitional cell carcinoma (TCC) of the bladder is the most common urothelial malignancy of the urinary tract, with an incidence of approximately 51,000 each year in the United States alone.

One reason that bladder cancer is so serious is because, presently, detecting and treating bladder cancer is difficult. Seventy percent of patients with an initial diagnosis of trrnsitional cell carcinoma have superficial tumors, which can be treated by transurethral resection alone. Approximately 70% of these patients continue to suffer from recurrent disease, and 15% develop lesions that invade muscle within the first two years.

Detecting tumor recurrence in patients with transitional cell carcinoma of the bladder requires close surveillance. Urine cytology is a common non-invasive procedure for the diagnosis of this disease, but it can miss up to 50% of tumors. The "gold standard" for diagnosis is cystoscopy, which allows visualization and direct biopsies of suspicious bladder lesions in the mucosa. However, because cystoscopy is an expensive and invasive procedure, it cannot be used as a general screening tool for the detection of bladder cancer.

Other serious cancers are the head and neck cancers. Head and neck cancer remains a morbid and often fatal disease. Large tumor bulk and tumor extension are predictors of a local regional recurrence and poor outcome. Detection of occult neoplastic cells in surrounding surgical margins is a strong predictor of local regional recurrence resulting in a significant decrease in overall survival DNA contains unique sequences interspersed with moderately and highly repetitive DNA sequences. Variations in the repetitive sequence elements such as minisatellite (or variable number tandem repeat) DNA sequences and microsatellite (or variable simple sequence repeat) DNA sequences have been useful for chromosomal identification, primary gene mapping, and linkage analysis. Microsatellite DNA sequences are an especially common and highly polymorphic class of genomic elements in the human genome. One advantage to the use of repetitive sequence variations is the greater number of alleles present in populations compared with unique genetic sequence variations. Another advantage is the ability to readily detect sequence length variations using the polymerase chain reaction for the rapid and inexpensive analysis of many DNA samples.

Tumors progress through a series of genetic mutations. These genetic mutations can be used as specific markers for the detection of cancer. One set of genetic mutations that can be used to detect the presence of cancer is the loss of chromosomes. Diploid organisms, including humans, have pair of chromosomes for each member of the chromosomal set. Tumor cells will characteristically lose chromosomes, resulting in a single chromosome, rather than a pair of chromosomes, for each member of the chromosomal set. Chromosomal deletions and additions are an integral part of neoplastic progression and have been described in most kinds of cancers. A pair of chromosomes which has two alleles for a genetic locus is heterozygous for that locus; therefore, heterozygosity correlates with a cell having a pair of chromosomes. For years, these chromosomal deletions or amplifications were detected through the loss of heterozygosity.

Another of the genetic mutations used to detect the presence of cancer is genetic instability. Genetic recombination tends to occur most frequently at regions of the chromosome where the DNA is homologous (where the DNA has a high degree of sequence similarity). Where a DNA sequence is repetitive, the DNA homology is greater. The DNA homology occurs not only at the same genetic locus on the other pair of chromosomes, but also on other genetic loci or within the same locus on the same chromosome. Normal (non-tumor) cells tend to suppress this genetic recombination. Tumor cells, however, characteristically undergo increased genetic recombination. Where a DNA sequence is repetitive, genetic recombination can result in the loss of repeat DNA sequences or the gain of repeat DNA sequences at a genetic locus.

Microsatellite DNA instability has been described in human cancers. Microsatellite DNA instability is an important feature of tumors from hereditary non-polyposis colorectal carcinoma patients Peltomäki et al., *Science*, 260: 810 (1993); Aaltonen et al., *Science*, 260: 812 (1993); Thibodeau et al., *Science*, 260: 816 (1993)). Microsatellite DNA instability by expansion or deletion of repeat elements has also been reported in colorectal, endometrial, breast, gastric, pancreatic, and bladder neoplastic tissues (Risinger et al., *Cancer Res.*, 53: 5100 (1993); Had et al., *Cancer Res.*, 53: 5087 (1993); Peltomäki et al., *Cancer Res.*, 53: 5853 (1993); Gonzalez-Zulueta et al., *Cancer Res.*, 53: 5620 (1993)).

Some methods have been developed to detect the multiple genetic changes that occur during the development of primary bladder cancer. For example, mutations in the tumor suppressor gene p53 signal the progression to invasiveness and have been successfully used as molecular markers to detect cancer cells in urine samples. However, this diagnostic strategy has limited clinical application because the techniques are cumbersome and because p53 mutations appear relatively late in the disease.

Because early diagnosis of bladder cancer is critical for successful treatment, there is a pressing need for more sensitive and cost-effective diagnostic tools. Both patients and physicians would benefit from the development of improved non-invasive methods for cancer surveillance.

SUMMARY OF THE INVENIION

The present invention provides a fast, reliable, sensitive and non-invasive screening method for the detection of a cell proliferative disorder in a subject. The method detects an allelic imbalance by assaying microsatellite DNA, wherein an abnormality in an allele is indicative of an allelic imbalance. Such abnormalities include an increase or decrease in microsatellite DNA that is at or corresponds to an allele. A decrease can be detected such that the level of DNA corresponding to the allele is less than 50% of the level of DNA of a corresponding allele in a microsatellite DNA sample of a subject that lacks the cell proliferative disorder.

The cell proliferative disorder detected by the method of the invention may be a neoplasm, for example, a neoplasm of the head, neck, lung, esophageal, stomach, small bowel, colon, bladder, kidney, or cervical tissue. The sample of microsatellite DNA may be urine, sputum, bile, stool, cervical tissue, saliva, tears, cerebral spinal fluid, serum, plasma, or lymphocytes, for example.

The microsatellite DNA detected by the method may be a locus such as DRPLA, UT762, IFNA, D9S200, D9S156, D3S1284, D3S1238, CHRNB1, D17S86, D9S747, D9S171, D16S476, D4S243, D14S50, D21S1245, FgA, D8S3G7, THO, D115488, D135802, D175695, D175654, and D20548.

The invention also provides a fast, reliable, sensitive and non-invasive screening method for detecting genetic instability of microsatellite DNA. An amplification or deletion of the small tandem repeat DNA sequences indicates genetic instability in the microsatellite DNA that is at or corresponds to an allele.

The present invention also provides a kit for detecting a cell proliferative disorder, comprising oligonucleotide primers that are complementary to a nucleotide sequence that flanks nucleotide repeats of microsatellite DNA. In one embodiment, the kdt further comprises a detectably labeled deoxyribonucleotide.

BRIEF DESCRIPTION OF THE DRAWINGS

FIG. 1 is a table of patients with bladder lesions and urine analysis (Cyto, cytology; LOH, loss of heterozygosity; Alt, microsatellite).

FIG. 2 is a table of microsatellite analysis of urine sediment.

FIG. 3 is a table of microsatellite analysis and clinical outcome in head and neck cancer patients.

FIG. 4 is a table of microsatellite analysis of patients with alterations in plasma.

FIG. 5 is a table of cytology and molecular status of patients with bladder cancers.

DETAILED DESCRIPTION OF THE INVENTION

The present invention relates to a non-invasive method for the detection of a cell proliferative disorder associated with mutations of microsatellite DNA in a subject. The invention provides a method for detecting an allelic imbalance by assaying microsatellite DNA. The invention also provides a method for detecting genetic inssbility of microsatellite DNA. The present invention is based on the three following principles:

First, chromosomal deletions and genetic recombination are an integral part of neoplastic progression and have been described in most kinds of cancers. Allelic imbalance (loss of heterozygosity) and genetic instability can now be detected in clinical samples composed mostly of normal-looking (morphologically normal) cells. The clinical samples can be readily obtained, thus providing a non-invasive alternative to surgery and microdissection of neoplastic tissue.

Second, monoclonality is a fundamental characteristic of neoplasms. Clonal genetic mutations are integrally involved in the progression of all cancers. Detection of a clonal population of cells harboring a chromosomal deletion or amplification is synonymous with the detection of cancer at a molecular level.

Third, microsatellite DNA in clinical samples can be amplified in vitro to detect an allelic imbalance (loss of heterozygosity) or genetic instability of microsatellite DNA. A combination of markers for each tumor type can now be used to identify many tumors in a given clinical sample. Moreover, these markers can also be multiplexed in a single amplification reaction to generate a low cost, reliable cancer screening test for many cancers simultaneously.

In one embodiment, the invention provides a method for detecting a cell proliferative disorder in a subject by detecting, in a sample of microsatellite DNA from the subject, an allelic imbalance. The presence of an allelic imbalance is indicative of a cell proliferative disorder.

The term "cell-proliferative disorder" includes both benign and malignant cell populations that morphologically differ from the surrounding tissue. For example, the method is useful for detecting tumors of the lung, breast, lymphoid, gastrointestinal, and genitourinary tract; epithelial carcinomas that include malignancies such as most colon cancers, renal-cell carcinoma, prostate cancer, non-small cell carcinoma of the lung, cancer of the small intestine, stomach cancer, kidney cancer, cervical cancer, cancer of the esophagus, and any other organ type that has a draining fluid or tissue accessible to analysis; and nonmalignant cell-proliferative diseases such as colon adenomas, hyperplasia, dysplasia and other pre-malignant lesions. Any disorder that is etiologically linked to mutations in a microsatellite DNA locus is susceptible to detection. In one embodiment, the method of the invention is usefuil for the detection of transitional cell carcinoma of the bladder and for the detection of head and neck cancer.

A cell proliferative disorder as described herein may be a neoplasm. Such neoplasms are either benign or malignant The term "neoplasm" refers to a new, abnormal growth of cells or a growth of abnormal cells that reproduce faster than normal. A neoplasm creates an unstructured mass (a tumor) which can be either benign or malignant. For example, the neoplasm may be a head, neck, lung, esophageal, stomach, small bowel, colon, bladder, kidney, or cervical neoplasm. The term "benign" refers to a tumor that is noncancerous, e.g. its cells do not proliferate or invade surrounding tissues. The term "malignant" refers to a tumor that is metastastic or no longer under normal cellular growth control.

The term "allelic imbalance" refers to the chromosomal loss or gain that is characteristic of tumor cells. Diploid organisms, including humans, have a pair of chromosomes for each member of the chromosomal set. Tumor cells characteristically lose chromosomes, often resulting in a single chromosome, rather than a pair of chromosomes, for each member of a chromosomal set. Tumor cells also on occasion gain chromosomes, resulting in a two or more chromosomes, rather than a pair of chromosomes, for each member of the chromosomal set.

When a genetic locus on the chromosome has a different DNA sequence on each chromosome, a diploid organism has two alleles for that genetic locus. A pair of chromosomes with two alleles for a genetic locus is heterozygous. Whether a genetic locus is heterozygous for a subject can readily be determined by analyzing a sample of DNA from the normal (non-tumor) cells of the subject. Because microsatellite DNA is polymorphic, a genetic locus that contains microsatellite DNA will frequently be heterozygous. When a tumor cell loses or gains a chromosome, the result is that the cell loses or gains an additional copy of one of the alleles, causing an allelic imbalance (loss of heterozygosity).

Microsatellite DNA markers that are heterozygous in normal (non-tumor) cell DNA can be used to detect mutations in tumor cell DNA. The loss of one allele identifies chromosomal deletions after gel electrophoresis or other techniques. An imbalance between the two alleles also identifies chromosomal amplifications. To do these analyses by conventional methods requires extensive microdissection of neoplastic cells so that normal (non-tumor) contaminating cells would not disrupt the assay. The method of the invention, by contrast, provides a non-invasive sampling technique in which the presence of normal (non-tumor) cells does not interfere with the assay. A loss of heterozygosity correlating with bladder cancer can be detected in urine samples in patients where the samples contain both normal and tumor cells. A loss of heterozygosity can be detected in the plasma and saliva of patients with head and neck cancer.

A combination of microsatellite DNA markers may be amplified in a single amplification reaction. The markers are multiplexed in a single amplification reaction, for example, by combining primers for more than one locus. For example, DNA from a urine sample can be amplified with three different randomly labeled primer sets, such as those used for the amplification of the FgA, ACTBP2 and AR loci, in the same amplification reaction. The reaction products are separated on a denaturing polyacrylamide gel, for example, and then exposed to film for visualization and analysis.

The term "microsatellite DNA" refers to mononucleotide, dinucleotide, or trinucleotide sequences where alleles differ by one or more repeat units. Microsatellite DNA is an especially common and highly polymorphic class of genomic elements in the human genome. The microsatellite DNA most preferred in the method of the invention has a sequence $(X)_n$, wherein X is the number of nucleotides in the repeat sequence and is greater than or equal to 1, preferably greater than or equal to 2, and most preferably greater than or equal to 3 and wherein n is the number of repeats and is greater than or equal to 2, and preferably from 4 to 6. When X is 2, the nucleofide sequence may be TC. When X is 3, the nucleotide sequence may be selected from AGC, TCC, CAG, CAA, and CTG. Two examples of trinucleotide repeats are D1S50 and DRPLA markers. Preferably when X is 4, the nucleotide sequence may be selected from AAAG, AGAT and TCTT. Two examples of tetranucleotide repeats are included in D21S1245 and FgA markers.

The microsatellite DNA sequence may be genetically linked to a unique locus. For example, microsatellite DNA mutations may be detected using a marker selected from ARA (chromosome X), D14S50 (chromosome 14), AR (chromosome X), MD (chromosome 19), SAT (chromosome 6), DRPLA (chromosome 12), ACTBP2 (chromosome 6), FgA (chromosome 4), D4S243 (chromosome 4), and UT762 (chromosome 21). Tandem repeat sequences have been identified as associated with Huntington's disease (HD), fragile X syndrome (FX), myotonic dystrophy (MD), spinocerebellar ataxia type I (SCA1), spino-bulbar muscular dystrophy, and hereditary dentatorubralpallidoluysian atrophy (DRPLA).

The term "sample of microsatellite DNA" refers to DNA present in or prepared from any tissue of a subject. The nucleic acid from any specimen, in purified or nonpurified form, can be used as the starting nucleic acid or acids, provided it contains, or is suspected of containing, the specific nucleic acid sequence containing the target nucleic acid. Thus, the process may employ, for example, DNA or RNA, including messenger RNA (mRNA). The DNA or RNA may be single stranded or double stranded. When RNA is used as a template, enzymes and conditions optimal for reverse transcribing the template to DNA would be used. A DNA-RNA hybrid that contains one strand of each may also be used. A mixture of nucleic acids may also be employed, or the nucleic acids produced in a previous amplification reaction herein, using the same or different primers may be so used. The mutant nucleotide sequence to be amplified may be a fraction of a larger molecule or can be present initially as a discrete molecule, such that the specific sequence is the entire nucleic acid. It is not necessary that the sequence to be amplified be present initially in a pure form; it may be a minor fraction of a complex mixture, such as contained in whole human DNA.

Samples or specimens include any microsatellite DNA sequence, whatever the origin, as long as the sequence is detectably present in a sample. While routine diagnostic tests may not be able to identify cancer cells in these samples, the non-invasive method of the present invention identifies neoplastic cells derived from the primary tumor. The sample of microsatellite DNA of the subject may be serum, plasma, lymphocytes, urine, sputum, bile, stool, cervical tissue, saliva, tears, cerebral spinal fluid, regional lymph node, histopathologic margins, and any bodily fluid that drains a body cavity or organ. Therefore, the method provides for the non-invasive detection of various tumor types including head and neck cancer, lung cancer, esophageal cancer, stomach cancer, small bowel cancer, colon cancer, bladder cancer, kidney cancers, cervical cancer and any other organ type that has a draining fluid accessible to analysis. For example, neoplasia of regional lymph nodes associated with a primary mammary tumor can be detected using the method of the invention. Regional lymph nodes for head and neck carcinomas include cervical lymph nodes, prelaryngeal lymph nodes, pulmonary juxtaesophageal lymph nodes and submandibular lymph nodes. Regional lymph nodes for mammary tissue carcinomas include the axillary and intercostal nodes. Samples also include urine DNA for bladder cancer or plasma or saliva DNA for head and neck cancer patients.

The method of the invention can also be used to detect a microsatellite DNA sequences associated with a primary tumor by assaying the surrounding tumor margin. A "tumor margin" as used herein refers to the tissue surrounding a discernible tumor. In the case of surgical removal of a solid tumor, the tumor margin is the tissue cut away with the discernible tumor that appears normal to the naked eye.

An allelic imbalance may be detected as a decrease in the level of DNA corresponding to an allele. The term "decrease in the level of DNA" refers to the observed difference of the ratio between the two alleles for a genetic locus. A sample of cells can have a ratio approaching 1:1 for a subject that lacks the cell proliferative disorder. The actual ratio for a subject can readily be determined by analyzing the DNA from the normal (non-tumor) cells of the tested subject. The level of DNA corresponding to the allele may be less than 50% of the level of DNA of a corresponding allele in a microsatellite DNA sample of a subject that lacks the cell proliferative disorder.

An allelic imbalance may also be detected as an increase in the level of DNA corresponding to an allele. The term "increase in the level of DNA" refers to the observed difference of the ratio between the two alleles for a genetic locus. A sample of cells will have a ratio that approaches 1:1 for a subject that lacks the cell proliferative disorder. Analyzing the DNA from the normal (non-tumor) cells of a test subject can readily determine the actual ratio for the subject.

An increase in the level of DNA may be detected as the appearance of a new allele. The term "presence of a new allele" refers both to the observed difference of the ratio between the two alleles for a genetic locus and to genetic instability, the genetic recombinations that are characteristic of tumor cells and that result in nucleic acid mutations as described infra. When there has been an increase in the number of chromosomes for a member of the chromosomal set, one of the chromosomes may undergo genetic recombination, so that there will be an addition or deletion of DNA repeats in the microsatellite DNA sequence. The mutated microsatellite DNA sequence is therefore a new allele for that genetic locus, as compared with the normal (non-tumor) cells of the subject. For example, a tumor cell may have three or more different alleles for a genetic locus instead of the two alleles found in the normal (non-tumor) cells. For another example, the presence of a new allele may correspond to the loss of an allele found in normal (non-tumor) cells.

Detection of an allelic imbalance may be performed by standard methods such as size fractionating the DNA. The term "size fractionating the DNA" refers to the separation of individual DNA molecules according to the size of the molecule. Methods of fractionating the DNA are well known to those of skill in the art. Fractionating the DNA on the basis of size may be accomplished by gel electrophoresis, including polyacrylamide gel electrophoresis (PAGE). For example, the gel may be a denaturing 7 M or 8 M ureapolyacrylamide-formamide gel. Size fractionating the DNA may also be accomplished by chromatographic methods known to those of skill in the art.

The reaction products containing microsatellite DNA may optionally be radioactively labeled. Any radioactive label may be employed which provides an adequate signal. Other labels include ligands, which can serve as a specific binding pair member for a labeled ligand, and the like. The labeled preparations are used to probe nucleic acid by the Southern hybridization technique, for example. Test nucleotide fragments are transferred to filters that bind nucleic acid. After exposure to the labeled microsatellite DNA probe, which will hybridize to nucleotide fragments containing target nucleic acid sequences, the binding of the radioactive probe to target nucleic acid fragments is identified by autoradiography (see *Genetic Engineering*, 1, ed. Robert Williamson, Academic Press (1981), pp. 72–81). The particular hybridization technique is not essential to the invention. Several hybridization techniques are well known or easily ascertained by one of ordinary skill in the art. As improvements are made in hybridization techniques, they can readily be applied in the method of the invention. This technique provides a further method of identification that can be additional or an alternative to size fractionation.

The microsatellite DNA may be amplified before detecting. The term "amplified" refers to the process of making multiple copies of DNA from a single molecule of DNA by genetic duplication. The amplification of DNA may occur in vivo by cellular mechanisms. The amplification of DNA may also occur in vitro by biochemical processes known to those of skill in the art. The amplification agent may be any compound or system that will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes that perform primer extension after being subjected to temperatures sufficiently elevated to cause denaturation). Suitable enzymes will facilitate combination of the nucleotides in the proper manner to form the primer extension products that are complementary to each mutant nucleotide strand. Generally, the synthesis will be initiated at the 3' end of each primer and proceed in the 5' direction along the template strand, until synthesis terminates, producing molecules of different lengths. There may be amplification agents, however, that initiate synthesis at the 5' end and proceed in the other direction, using the same process as described above. In any event, the method of the invention is not to be limited to the embodiments of amplification described herein.

One method of in vitro amplification which can be used according to this invention is the polymerase chain reaction (PCR) described in U.S. Pat. Nos. 4,683,202 and 4,683,195. The term "polymerase chain reaction" refers to a method for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. The polymerase chain reaction is used to detect the existence of the defined sequence in the microsatellite DNA sample. Many polymerase chain methods are known to those of skill in the art and may be used in the method of the invention. For example, DNA can be subjected to 30 to 35 cycles of amplification in a thermocycler as follows: 95° C. for 30 sec, 52° to 60° C. for 1 min, and 72° C. for 1 min, with a final extension step of 72° C. for 5 min. For another example, DNA can be subjected to 35 polymerase chain reaction cycles in a thermocycler at a denaturing temperature of 95° C. for 30 sec, followed by varying annealing temperatures ranging from 54–58° C. for 1 min, an extension step at 70° C. for 1 min and a final extension step at 70° C.

Exemplary target nucleotide sequences of the invention, to which complementary oligonucleotide primers hybridize, include the following:

```
SEQ ID NO:1
5'-CTTGTGTCCCGGCGTCTG-3'

SEQ ID NO:2
5'-CAGCCCAGCAGGACCAGTA-3'

SEQ ID NO:3
5'-TGGTAACAGTGGAATACTGAC-3'

SEQ ID NO:4
5'-ACTGATGCAAAAATCCTCAAC-3'

SEQ ID NO:5
5'-GATGGGCAAACTGCAGGCCTGGGAAG-3'

SEQ ID NO:6
5'-GCTACAAGGACCCTTCGAGCCCCGTTC-3'

SEQ ID NO:7
5'-GATGGTGATGTGTTGAGACTGGTG-3'

SEQ ID NO:8
```

-continued

SEQ ID NO:8
5'-GAGCATTTCCCCACCCACTGGAGG-3'

SEQ ID NO:9
5'-GTTCTGGATCACTTCGCGGA-3'

SEQ ID NO:10
5'-TGAGGATGGTTCTCCCCAAG-3'

SEQ ID NO:11
5'-AGTGGTGAATTAGGGGTGTT-3'

SEQ ID NO:12
5'-CTGCCATCTTGTGGAATCAT-3'

SEQ ID NO:13
5'-CTGTGAGTTCAAAACCTATGG-3'

SEQ ID NO:14
5'-GTGTCAGAGGATCTGAGAAG-3'

SEQ ID NO:15
5'-GCACGCTCTGGAACAGATTCTGGA-3'

SEQ ID NO:16
5'-ATGAGGAACAGCAACCTTCACAGC-3'

SEQ ID NO:17
5'-TCACTCTTGTCGCCCAGATT-3'

SEQ ID NO:18
5'-TATAGCGGTAGGGGAGATGT-3'

SEQ ID NO:19
5'-TGCAAGGAGAAAGAGAGACTGA-3'

SEQ ID NO:20
5'-AACAGGACCACAGGCTCCTA-3'

SEQ ID NO:21
5'-TCTCTTTCTTTCCTTGACAGGGTC-3'

SEQ ID NO:22
5'-CAGTGTGGTCCCAAATTTGAAATGG-3'

SEQ ID NO:23
5'-GTGCTGACTAGGGCAGCTT-3'

SEQ ID NO:24
5'-TGTGACCTGCACTCGGAAGC-3'

SEQ ID NO:25
5'-CCTTTCCTTCCTTCCTTCC-3'

SEQ ID NO:26
5'-CACAGTCAGGTCAGGCTATCAG-3'

SEQ ID NO:27
5'-TTTTTGAGATAGAGTCTCACTGTG-3'

SEQ ID NO:28
5'-CCACAGTCTAAGCCAGTCTGA-3'

SEQ ID NO:29
5'-GAATTTTGCTCTTGTTGCCCAG-3'

SEQ ID NO:30
5'-AGACTGAAGTCAATGAACAACAAC-3'

SEQ ID NO:31
5'-GGCTGTGAACATGGCCTAGGTC-3'

SEQ ID NO:32
5'-TTGGGGTGGTGCCAATGGATGTC-3'

SEQ ID NO:33
5'-CAGACGCCGGGACACAAG-3'

SEQ ID NO:34
5'-TACTGGTCCTGCTGGGCTG-3'

-continued

SEQ ID NO:35
D21S1245(F) 5'-GTCAGTATTACCCTGTTACCA-3'

SEQ ID NO:36
D21S1245(R) 5'-GTTGAGGATTTTTGCATCAGT-3'

SEQ ID NO:37
5'-CTTCCCAGGCCTGCAGTTTGCCCATC-3'

SEQ ID NO:38
5'-GAACGGGGCTCGAAGGGTCCTTGTAGC-3'

SEQ ID NO:39
DRPLA(F) 5'-CACCAGTCTCAACACATCACCATC-3'

SEQ ID NO:40
DRPLA(R) 5'-CCTCCAGTGGGTGGGAAATGCTC-3'

SEQ ID NO:41
5'-TCCGCGAAGTGATCCAGAAC-3'

SEQ ID NO:42
5'-CTTGGGGAGAACCATCCTCA-3'

SEQ ID NO:43
D14S50(F) 5'-AACACCCCTAATTCACCACT-3'

SEQ ID NO:44
D14S50(R) 5'-ATGATTCCACAAGATGGCAG-3'

SEQ ID NO:45
FgA(F) 5'-CCATAGGTTTTGAACTCACAG-3'

SEQ ID NO:46
FgA(R) 5'-CTTCTCAGATCCTCTGACAC-3'

SEQ ID NO:47
D20S48(F) 5'-TCCAGAATCTGTTCCAGAGCGTGC-3'

SEQ ID NO:48
D20S48(R) 5'-GCTGTGAAGGTTGCTGTTCCTCAT-3'

SEQ ID NO:49
5'-AATCTGGGCGACAAGAGTGA-3'

SEQ ID NO:50
5'-ACATCTCCCCTACCGCTATA-3'

SEQ ID NO:51
5'-TCAGTCTCTCTTTCTCCTTGCA-3'

SEQ ID NO:52
5'-TAGGAGCCTGTGGTCCTGTT-3'

SEQ ID NO:53
D8S3G7(F) 5'-GACCCTGTCAAGGAAAGAAAGAGA-3'

SEQ ID NO:54
D8S3G7(R) 5'-CCATTTCAAATTTGGGACCACACTG-3'

SEQ ID NO:55
THO(F) 5'-AAGCTGCCCTAGTCAGCAC-3'

SEQ ID NO:56
THO(R) 5'-GCTTCCGAGTGCAGGTCACA-3'

SEQ ID NO:57
D11S488(F) 5'-mGGAAGGAAGGAAGGAAAGG-3'

SEQ ID NO:58
D11S488(R) 5'-CTGATAGCCTGACCTGACTGTG-3'

SEQ ID NO:59
D13S802(F) 5'-CACAGTGAGACTCTATCTCAAAAA-3'

SEQ ID NO:60
D13S802(R) 5'-TCAGACTGGCTTAGACTGTGG-3'

SEQ ID NO:61
D17S695(F) 5'-CTGGGCAACAAGAGCAAAATTC-3'

-continued

SEQ ID NO:62
D175695(R) 5'-mGTTGTTGTTCATTGACTTCAGTCT-3'

SEQ ID NO:63
D175654(F) 5'-GACCTAGGCCATGTTCACAGCC-3'

SEQ ID NO:64
D175654(R) 5'-GACATCCATTGGCACCACCCCAA-3'

Those of ordinary skill in the art will know of various amplification methodologies which can also be utilized to increase the copy number of target nucleic acid. Microsatellite DNA sequence detected in the method of the invention can be further evahlated, detected, cloned, sequenced, and the like, either in solution or after binding to a solid support, by any method usually applied to the detection of a specific DNA sequence such as another polymerase chain reaction, oligomer restriction (Saiki et al., Bio/Technology 3: 1008–1012 (1985)), allele-specific oligonucleotide (ASO) probe analysis (Conner et al., Proc. Natl. Acad. Sci. USA 80: 278 (1983), oligonucleotide ligation assays (OLAs) (Landegren et al., Science 241: 1077 (1988)), and the like. Molecular techniques for DNA analysis have been reviewed (Landegren et al, Science, 242: 229–237 (1988)). Following DNA amplification, the reaction product may be detected by Southern blot analysis, without using radioactive probes. In such a process, for example, a small sample of DNA containing a very low level of microsatellite DNA nucleotide sequence is amplified, and analyzed via a Southern blotting technique. The use of non-radioactive probes or labels is facilitated by the high level of the amplified signal. In a preferred embodiment of the invention, one nucleoside triphosphate is radioactively labeled, thereby allowing direct visualization of the amplification product by autoradiography. In another embodiment, amplification primers are fluorescent labeled and run through an electrophoresis system. Visualization of amplified products is by laser detection followed by computer assisted graphic display.

In another embodiment, the invention is a method for detecting a cell proliferative disorder in a subject. The method detects genetic isstbiity in a sample of microsatellite DNA of the mammal as an indication of a cell proliferative disorder. As used herein, the term "genetic instability" refers to genetic recombinations which are characteristic of tumor cells and which result in nucleic acid mutations. Such mutations include the deletion and addition of nucleotides. The genetically unstable sequences of the invention are preferably microsatellite DNA sequences which, by definition, are small tandem repeat DNA sequences.

Genetic recombination tends to occur most frequently at regions of the chromosome where the DNA is homologous (where the DNA has a high degree of sequence similarity). Where a DNA sequence is repetitive, the DNA homology is greater. The DNA homology occurs not only at the same genetic locus on the other pair of chromosomes, but also on other genetic loci or within the same locus on the same chromosome. In normal (non-tumor cells) this genetic recombination tends to be suppressed. Tumor cells, however, characteristically undergo increased genetic recombination. Where a DNA sequence is repetitive, genetic recombination can result in the loss of repeat DNA sequences or the gain of repeat DNA sequences at a genetic locus.

When the microsatellite DNA repeat is larger, it is more likely that the microsatellite DNA locus will have mutations. A trinucleotide repeat is more likely to have deletions or additions than a dinucleotide repeat. A regular repeat, such as AATAATAAT is more likely to have mutations than a sequence which contains interruptions in the repeat sequence, e.g., AATGACAATAAT. Consequently, those of ordinary skill in the art can readily identify other target nucleic acid sequences by considering the size of the candidate sequence and whether the sequence is uninterrupted without resorting to undue experunentation Other microsatellite DNA markers will be known by the criteria described herein and are accessible to those of skill in the art. Smaller microsatellite DNA markers including dinucleotide and mononucleotide repeats will also be useful for this analysis.

The genetic instability may be detected as an amplification of nucleotide repeats in the DNA. The term "amplification of nucleotide repeats" refers to a mutation in the sequence of the microsatellite DNA wherein the resulting microsatellite DNA sequence has more DNA repeats than the sequence found in normal (non-tumor) cells. Where the normal cell microsatellite DNA has a sequence $(X)_{n1}$, X is the number of nucleotides, and n1 and n2 are numbers of repeats, the resulting microsatellite DNA sequence is $(X)_{n1+n2}$.

The instability may be detected as a deletion of nucleotide repeats in the DNA. The term "deletion of nucleotide repeats" refers to a mutation in the sequence of the microsatellite DNA wherein the resulting microsatellite DNA sequence has fewer DNA repeats than the sequence found in normal (non-tumor) cells. Where the normal cell microsatellite DNA has a sequence $(X)_{n1}$, X is the number of nucleotides, n1 and n2 are numbers of repeats, and n1 is greater than n2, the resulting microsatellite DNA sequence is $(X)_{n1-n2}$.

The instability may be detected when the DNA is amplified before detecting. The amplification may be accomplished by the polymerase chain reaction, as described supra. Those of skill in the art will know of other amplification methods which can increase the copy number of target nucleic acid.

The genetic instability may be detected when the cell proliferative disorder is not due to a repair gene defect. The term "repair gene defect" refers to a defect in a gene coding for any of a number of processes to repair damaged DNA. In gene repair, the damaged portions of the DNA molecule are removed by enzymes (each enzyne coded for by a repair gene), leaving holes where bases should be. Then other enzymes (also coded for by repair genes) remove an entire segment of DNA, in the middle of which was the hole or holes. A DNA polymerase (coded for by repair genes) then fills the gap with nucleotide bases, based on what bases are on the opposite strand of DNA. Finally a ligase enzyme (coded for by repair genes) seals the phosphate backbone back together.

Another type of DNA repair is error-prone repair (SOS repair), which occurs when both nucleotides in a base pair are missing, such that it is not possible to maintain accuracy. The enzymes and other proteins which mediate error-prone repair are coded for by repair genes. Still another type of DNA repair is excision repair, where the damaged portion of DNA is excised, or removed, then the removed part is recopied from the other undamaged strand by DNA polymerase enzymes, and fmally the replacement part is attached to the site by DNA ligase enzymes. The enzymes and other proteins which mediate excision repair are also coded for by repair genes.

Those of skill in the art will be familiar with those genes which code for the processes which repair damaged DNA.

Those of skill in the art will also be able to identify these genes by their chromosomal location and by the methods of DNA amplification and size fractionation.

The genetic instability may be detected when the cell proliferative disorder is a neoplasm. Neoplasms are described supra.

The microsatellite DNA may be from a locus that has been used in genetic mapping. Among the loci may be one or more of the following: DRPLA, UT762, IFNA, D9S200, D9S156, D3S1284, D3S1238, CHRNB1, D17S86, D9S747, D9S171, D16S476, D4S243, D14S50, C21S1245, FgA, D8S3G7, THO, D11S488, D13S802, D17S695, D17S654, and D20S48.

The term "oligonucleotide primer" refers to a sequence of two or more deoxyribonucleotides or ribonucleotides, preferably at least eight, which sequence is capable of initiating synthesis of a primer extension product that is substantially complementary to a target nucleic acid strand. The oligonucleotide primer typically contains fifteen to twenty-two or more nucleotides, although it may contain fewer nucleotides if the primer is complementary, so as to specifically allow the amplification of the specifically desired target nucleotide sequence.

The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage et al., *Tetrahedron Letter*, 22: 1859–1862 (1981). One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the method of the invention are complementary to each strand of mutant nucleotide sequence to be amplified. The term "complementary" means that the primers must hybridize with their respective strands under conditions which allow the agent for polymerization to function. In other words, the primers that are complementary to the flanking sequences hybridize with the flanking sequences and permit amplification of the nucleotide sequence. Preferably, the 3' terminus of the primer that is extended has perfectly base paired complementarity with the complementary flanking strand.

The term "flanks nucleotide repeats" refers to those DNA sequences on chromosome that are upstream (5') or downstream (3') to the DNA sequence to be amplified. The nucleotide repeat sequence to be amplified is preferably a microsatellite DNA sequence. For example, when the nucleotide repeat sequence to be amplified is double stranded, a first sequence that is 5' to the nucleotide repeat sequence and a second sequence that is 5' to the nucleotide repeat sequence on the complementary strand flank the microsatellite DNA sequence.

The nucleotide sequences that flank nucleotide repeats, i.e., the nucleotide sequences to which the oligonucleotide primers hybridize, may be selected from among the following nucleotide sequences: SEQ ID NO:1–32.

When it is desirable to amplify the target nucleotide sequence, such as a microsatellite DNA sequence, before detection, oligonucleotides can be used as the primers for amplification. The oligonucleotide primers are designed based upon identification of the nucleic acid sequence of the flanking regions contiguous with the microsatellite DNA. One skilled in the art will be able to generate primers suitable for amplifying target sequences of additional nucleic acids, such as those flanking loci of known microsatellite DNA sequences, using routine skills known in the art and the teachings of this invention.

The oligonucleotide primers used in the amplification may be selected from among the following primers: SEQ ID NO:33–64.

In another embodiment, the invention provides a kit for detecting a mammalian cell proliferative disorder. The kit comprises an oligonucleotide primer that is complementary to a nucleic acid sequence that flanks nucleotide repeats of microsatellite DNA. Such a kit may also include a carrier means being compartmentalized to receive in close confinement one or more containers such as vials, tubes, and the like, each of the containers comprising one of the separate elements to be used in the method. For example, one of the containers may include amplification primers for a microsatellite DNA locus or a hybridization probe, all of which can be detectably labeled. If present, a second container may comprise a lysis buffer.

The kit may also have containers containing nucleotides for amplification of the target nucleic acid sequence which may or may not be labeled, or a container comprising a reporter, such as a biotin-binding protein, such as avidin or streptavidin, bound to a reporter molecule, such as an enzymatic, florescent, or radionuclide label. The term "detectably labeled deoxyribonucleotide" refers to a means for identifying deoxyribonucleotide. The detectable label may be a radiolabeled nucleotide. The detectable label may be a small molecule covalently bound to the nucleotide where the small molecule is recognized by a well-characterized large molecule. Examples of these small molecules are biotin, which is bound by avidin, and thyroxin, which is bound by anti-thyroxin antibody. Other methods of labeling are known to those of ordinary skill in the art, including fluorescent compounds, chemilummescent compounds, phosphorescent compounds, and bioluminescent compounds.

In general, the primers used according to the method of the invention embrace oligonucleotides of sufficient length and appropriate sequence which provide specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Oligonucleotide primers used according to the invention are employed in any amplification process that produces increased quantities of target nucleic acid.

The above disclosure generally describes the present invention. A more complete understanding can be obtained by reference to the following specific examples. These examples are provided herein for purposes of illustration only and are not intended to limit the scope of the invention.

EXAMPLE 1

Molecular Detection of Primary Bladder Cancer by Microsatellite DNA Analysis

The purpose of this Example is to show that microsatellite DNA markers are useful as clonal markers for the detection of human cancer, because simple DNA repeat mutations can be readily detected in clinical samples by the polymerase chain reaction. In this Example, the feasibility of polymerase chain reaction-based microsatellite DNA analysis of DNA from urine sediment is shown by correctly identifying nineteen of twenty patients with primary bladder tumors by this approach. In contrast, using uDne cytology, only nme of eighteen affected patients were detected.

Sixty trinucleotide and tetrucleotide markers in the DNA from fifty anonymous primary bladder cancers were screened. The screening was done in the following manner: Frozen tumor tissue was cut into 10 µm sections. All samples, including lymphocytes, were digested with 1% SDS-proteinase K at 60° C. for 5 hr. DNA was extracted by ethanol precipitation. Urine samples were spun at 3000 g for 5 min and washed twice with phosphate-buffered saline. Each polymerase chain reaction mixture (25 µl) contained 50 ng of DNA template. Primers were obtained from Research Genetics (Huntsville, Ala.) or snthesized from sequences in the Genome Database. For microsatellite DNA analysis, one primer was labeled with T4 polynucleotide kinase (New England Biolabs) and [γ-$^{32}$P]-adenosine triphosphate (New England Nuclear). DNA was subjected to 30 to 35 cycles of amplification in a Hybaid (Middlesex, UK) Omnigene TR3 SM2 Thermocycler as follows: 95° C. for 30 sec, 52° to 60° C. for 1 min, and 72° C. for 1 min, with a final extension step of 72° C. for 5 min. Polymerase chain reaction products were separated by electrophoresis in denaturing 8 M urea-polyacrylamide-formamide gels, which were then subjected to autoradiography.

Of the screened primary bladder cancers, 40 (80%) contained at least one marker alteration when compared with the DNA from matched normal lymphocytes. Calculations showed that a panel of the ten most useful markers would theoretically detect mutations in 52% of all cancers. The calculation was done as follows: The total mutations for each marker tested in all tumors were tabulated and then grouped, in descending order, from the markers most susceptible in mutations that would empirically detect the greater number of primary tumors. Thus, the ten most susceptible markers empirically identified at least on alteration in twenty-six of fifty tumors (52%), eleven identified 56% of tumors, twelve identified 60%, thirteen identified 62%, and so forth. Some markers identified mutations only in tumors previously identified by another marker, and 20% of tumors did not demonstrate a single alteration with any marker tested.

Twenty-five patients who were screened for primary bladder cancers presented with symptoms suggestive of bladder cancer (for example, gross hematuria) and were found to harbor suspicious lesions at cystoscopy. Urine samples were collected (before cystoscopy) and were then distributed in blinded fashion for microsatellite DNA analysis and routine urine cytology. Then, the DNA in the urine sediment from these twenty-five patients with suspicious bladder lesions and from five controls (patients without evidence of bladder cancer) was tested. Urine and lymphocyte DNA from each patient were amplified by polymerase chain reaction, and polymorphic alleles were compared at the ten preselected microsatellite DNA loci. The urine DNA of ten patients contained a microsatellite DNA mutations (expansion or deletion of a repeat unit), in close agreement with the frequency expected on the basis of the calculations.

In addition to microsatellite DNA mutations, primary tumors often harbor chromosomal deletions at suppressor gene loci that are manifested as loss of heterozygosity and are readily detected by microsatellite DNA analysis. Notably, eighteen urine DNA samples also demonstrated loss of heterozygosity, particularly with marker D9S747 from chromosome 9p21. This result is consistent with the observation that loss of chromosome 9 occurs frequently in bladder cancer. Analysis of three additional dinucleotide markers on chromosome 9p21 (D9S171, D9S162, and IFNA) for loss of heterozygosity confirmed the presence of deletions in urine samples that demonstrated loss of chromosome 9 with marker D9S747.

That the genetically altered alleles were derived from exfoliated cancer cells was confinmed by two methods:

First, the primary tumors from biopsies of fifteen of the twenty cancer patients (in five cases, there was insufficient biopsy material for this analysis) were examined. In all patients, the same microsatellite DNA mutations and loss of heterozygosity patterns detected in the urine were also detected in the primary tumor. However, in two patients, the urine samples showed loss of heterozygosity or microsatellite DNA mutations that were not present in the biopsies. In both cases, loss of heterozygosity in at least one locus (and loss of the identical allele) was shared between the urine sediment and the primary tumor. Conceivably, the urine sample may have contained a more advanced tumor cell clone that was derived from the same progenitor cell but was not sampled by the small biopsy of the tumor.

Second, cells from the same urine samples were then examined by light microscopy. Cytologic analysis was performed in a blinded fashion, following normal clinical procedures in samples from eighteen of the twenty patients with bladder cancer and from three of the five patients with suspicious lesions but without neoplasia. Those normal clinical procedures are as follows: Approximately 50 cm$^3$ of urine was obtained and concentrated by centrifugation on cytospin glass slides or Millipore filters (Burlington, Mass.). Cells were stained by Papanicolaou stain and vsulized under microscopy. Standard morphologic criteria were used to establish the presence of neoplastic cells. Neoplastic cells were identified by cytology in nine of the eighteen patients for whom molecular analysis was positive and in one patient for whom molecular analysis was negative.

Twenty of the twenty-five patients had histologically confirmed bladder cancer. Overall, microsatellite DNA analysis with the thirteen markers detected genetic mutations in nineteen of these twenty cancer patient Of four patients with inflammation that prompted cystoscopy, two showed molecular changes (loss of heterozygosity, genetic instability, or both) in the urine, and both had bladder lesions containing atypical cells that were suspicious but not diagnostic for cancer. None of the five patients without neoplasia (controls) showed any microsatellite DNA mutations (see FIGS. 1 and 2).

This Example demonstrates that microsatellite DNA analysis can be a powerful tool in the detection of primary bladder cancer. The ease of loss of heterozygosity detection in urine sediment is consistent with analysis on urine samples by fluorescence in situ hybridization (FISH). Moreover, molecular analysis of patients with multiple tumors has demonstrated that these multiple tumors appeared to arise from a single progenitor cell that seeded and populated the bladder mucosa, potentially accounting for the high risk of recurrence in these patients. These observations are compatible with the hypothesis that large areas of transformed bladder mucosa can exist in patients with small neoplasms. Other factors may also contribute to the enrichment of tumor cells in urine; for example, more tumor cells than normal cells may survive storage. In addition, as tumor surfaces are composed of actively growing cell populations that clonally expand through mechanisms such as loss of adhesion, it is possible that these cells are more readily shed into the urine.

These microsatellite DNA markers enabled the detection of 95% of the bladder cancers in this study, but as new markers are identified, the approach can be expanded and improved. Despite an expected identification of only ~50% of cases, the identification of loss of heterozygosity in addition to microsatellite DNA mutations greatly improved the detection strategy. An adenocarcinoma of the prostatic fossa was also identified, indicating that markers commonly deleted in other genitourina tract neoplasm may facilitate the detection of other neoplasms that exfoliate cells into urine sediment.

Finally, our approach highlights the immediate utility of studies that demonstrate loss of heterozygosity in human cancer and of the development of molecular progression models for clinical detection. In most of the cases in this study, morphologic and cytologic analyses were not diagnostic. Molecular analysis reliably detected tumors of all grades and stages, including those often missed by cytology. In principle, this molecular approach can be performed at approximately one-third the cost of cytology and does not require exhaustive expert interpretation.

Moreover, the entire assay is amenable to nonradioactive, non-gel separation techniques and potentially could lead to a reliable, yet inexpensive, molecular screening test.

EXAMPLE 2

Microsatellite DNA Alterations in Serum DNA of Head and Neck Cancer Patients

The purpose of this Example is to show that microsatellite DNA analysis of serum represents a novel method for the detection of circulating tumor cell DNA. Lymphocyte, serum and tumor DNA were retrospectively analyzed from twenty-one head and neck cancer patients. Head and neck cancer remains a morbid and often fatal disease. Large tumor bulk and tumor extension are predictors of local regional recurrence and poor outcome. Molecular detection of occult neoplastic cells in surrounding surgical margins is a strong predictor of local regional recurrence resulting in a significant decrease in overall survival. In this Example, twenty-one patients were followed from initial diagnosis of transitional cell carcinoma with microsatellite DNA analysis of urine DNA at the time of cystoscopic evaluations scheduled at routine intervals. In almost all cases, DNA-based analysis correlated precisely with clinical findings at cystoscopy and subsequent histopathology. In two cases, DNA analysis correctly predicted the presence of a tumor several months before the lesion was detected during examination with a cystoscope.

These twenty-one patients were chosen from our tumor bank because all three DNA sources were available for complete analysis, and the serum samples had been collected before surgical resection of head and neck cancer. Twelve microsatellite DNA markers were selected to detect shifts of loss of heterozygosity. Eight markers were chosen on 9p, 3p and 17p, because these chromosomal arms show the highest percentage of loss of heterozygosity and appear to harbor tumor suppressor gene loci involved early in the progression of head and neck cancer. Furthermore, two trinucleotide (D1S50 and DRPLA) and two tetranucleotide (D21S1245 and FgA) markers, recognized as being prone to microsatellite DNA instability and located on loci commonly altered in cancers, were used in the study for increased sensitivity in the detection of shifts. Loss of heterozygosity was scored if the allele signal was reduced to less then 50% of control intensity. Shifts were called if there was an obvious new allele compared with normal (non-tumor) lymphocyte DNA.

Sample collection and DNA isolation was accomplished as follows: Tumors obtained fresh from surgical resection and blood by venipuncture from head and neck cancer patients were collected from patients at the Johns Hopkins University Medical Instiutions with prior consent. To obtain, serum, clotted blood specimens were centrifuged at low speed for 5 min, and the serum was stored at −80° C. before DNA extraction. Tumor tissue was frozen and microdissected. Lymphocytes, tumor tissue and serum were digested in SDS and proteinase K at 48° C. overnight, followed by phenol/chloroform extraction and ethanol precipitation of DNA. The mean concentration of DNA in the cancer patients was 110±50 ng per ml serum, and 10 μl was usually sufficient for robust microsatellite DNA analysis. The concentration of serum DNA from normal controls ranges from 0 to 100 ng/ml.

Polymerase chain reaction amplification was performed as follows: Oligonucleotide markers for microsatellite DNA analysis were obtained from Research Genetics (Huntsville, Ala.) and included IFNA, D9S156, D9S161, D9S200 on 9p; D3S1238, D3S1284 on 3p; D17S786 and CHRNB1 on 17p. Trinucleotide and tetranucleotide primers used included the following:

```
for D14S50:

D14S50(F)    5'-AACACCCCTAATTCACCACT-3' (SEQ ID NO:43)

D14S50(R)    5'-ATGATTCCACAAGATGGCAG-3' (SEQ ID NO:44)

for D21S1245:

D21S1245(F)  5'-GTCAGTATTACCCTGTTACCA-3' (SEQ ID NO:35)

D21S1245(R)  5'-GTTGAGGATTTTTGCATCAGT-3' (SEQ ID NO:36)

for DRPLA:

DRPLA(F)     5'-CACAGTCTCAACACATC-3' (SEQ ID NO:39)

DRPLA(R)     5'-CCTCCAGTGGGTGGGAAATGCCTC-3' (SEQ ID NO:40)

for FgA:
```

-continued

FgA(F)   5'-CCATAGGTTTTGAACTCACAG-3' (SEQ ID NO:45)

FgA(R)   5'-CTTCTCAGATTCCTTCTTGACAC-3' (SEQ ID NO:46)

One primer from each set was end labeled with ($\gamma$-$^{32}$P) ATP (Amersham) using T4 polynucleotide kiase (New England Biolabs). Polymerase chain reaction amplification was performed with 30–60 ng DNA was described previously. Products were separated in 8% denaturing urea-polyacrylamide-fonnamide gels followed by autoradiography. Loss of heterozygosity was called if the ratio of one allele was significantly decreased (>50%) in tumor or serum DNA compared with normal (non-tumor) lymphocyte DNA.

A tumor-specific microsatellite DNA shift, represented by a novel allele after gel electrophoresis, can still be seen when tumor DNA is diluted between 1:500 to 1:1000 with normal DNA. Shifts derived from primary tumor cell DNA in the serum might have been expected. However, there was a surprisingly clear loss of heterozygosity in serum DNA. The first patient that had such provocative results was an 80-year-old man diagnosed with $T_3N_cM_0$ glottic cancer who underwent a total laryngectomy in January 1993. He had no evidence of disease on three months' follow-up. However, in September 1993, he was diagnosed with recurrence of tumor in the right neck with the mass surrounding the right carotid artery, and he died of regional disease in November 1994. The senum DNA of this patient displayed a clear loss of heterozygosity. This result was unexpected and reminiscent of the clear loss of heterozygosity and shifts seen in the urine of patients diagnosed with bladder cancer.

After microsatellite DNA analysis of all specimens was completed, clinical data were correlated with the results. Clinical correlation was performed as follows: Clinical outcome data was obtained from the Johns Hopkins Head and Neck Cancer Tumor Registry and by chart review. Fisher's exact test was used to compare results from plasma analysis with clinical outcome parameters (see FIGS. 3 and 4).

All six patients that had microsatellite DNA mutations in the serum DNA demonstrated identical mutations in the primary tumor DNA Four out of six patients displayed mutations in more than one locus, and all of these patients had advanced disease (stage III–IV). In this small group, four patients went on to die from cancer, one patient has terminal cancer with metastases and one patient has no evidence of disease at three years' follow-up. Five patients had nodal metastases and three of them later developed distant metastases, one patient to lung and bone and the other two patients to lung and liver.

Conversely, another nine patients had advanced stage cancer, but no microsatellite DNA mutations in their serum DNA. Six of these patients had successful resections and were free of disease on long-term follow-up (more than one year); two of them died within two years diagnosis from regional recurrence and one was lost to follow-up. Seven of these patients, including those with a good prognosis, exhibited loss of heterozygosity or shifts in their primary tumor DNA but had no evidence of mutations in serum DNA Lack of positive findings in serum DNA was also seen in six out of twenty-one patients that had stage I and II cancer, all with good prognoses except for one patient who had a recurrence seven years later and died. Three patients displayed no microsatellite DNA mutations in their primary tumor DNA with the tested markers. The data are statistically significant for a positive serum test as predictor of future distant metastases by the Fisher's exact test (P=0.015); nevertheless, any conclusions of predictive ability or clinical utility require verification with larger populations and well-defined cohorts.

The results of this Example support the idea of tumor DNA enrichment in blood serum and plasma. Identification of clear loss of heterozygosity strongly favors the hypothesis that tumor DNA is enriched and, in fact, the predominant form of DNA in the plasma. Such analysis of plasma DNA will be useful in follow-up of cancer patients receiving medical or surgical treatment. Moreover, serum microsatellite DNA mutations were always identical to mutations in the primary tumor DNA. The higher frequency of plasma mutations in small cell lung cancer may reflect the much higher frequency of clinical metastases in SCLC patients compared with head and neck cancer patients. In bulky head and neck tumors, cell lysis by necrosis or even apoptosis leads to the release of naked DNA into the circulation. For large tumors, this phenomenon may occur more frequently because of local angiogenesis and necrosis. Although a surprising finding, tumor DNA readily survives in various bodily fluids including urine, stool and sputum.

EXAMPLE 3

Detection of Bladder Cancer Reoccurrence by Microsatellite DNA Analysis of Urine The purpose of this Example was to demonstrate that the microsatellite DNA analysis method can be used for following-up patients with transitional cell carcinoma. A reliable, non-invasive method for monitoring patients with transitional cell carcinoma of the bladder would be of great clinical benefit. In this Example, serial urine samples were tested from twenty-one patients who had been treated for bladder cancer with twenty polymorphic microsatellite DNA markers in a blinded fashion. Recurrent lesions were detected in ten out of eleven patients and correctly predicted the existence of a neoplastic cell population in the urine of two patients, four and six months before cystoscopic evidence of the tumor. The assay was negative in ten of ten patients who had no evident cancer. This Example shows that microsatellite DNA analysis of urine sediment represents a novel and potentially powerfuil clinical tool for the detection of recurrent bladder cancer.

The microsatellite DNA analysis was done as follows: DNA was tested from the urine of twenty-one patients with a panel of twenty microsatellite DNA markers immediately after the initial diagnosis of a prinary bladder tumor. This panel of markers comprised thirteen markers used in our initial study and seven additional selected markers. Eleven of these patients were tested in Example 1 and were included here for monitoring of tumor recurrence.

Initial urine samples (from before resection) were available from twenty of these twenty-one patients with transitional cell carcinoma. Tissue and urine specimens were performed as follows: Twenty patients with histologically confirmed bladder carcinoma and one patient with transitional cell carcinoma of the renal pelvis were enrolled into the study. Mean age at time of diagnosis was 68.2 years (50–86), the male/female ratio was 2:1, and the patients were followed for a mean of eight months (3–18) at our institution. Venous blood (10 ml) was obtained from every patient for extraction of normal (germline) DNA to be used as a control. Urine (50 ml) was collected from each patient before surgical intervention (transurethral resection or biopsy) and specimens from the initial surgery or biopsy were frozen at −70° C. immediately before each follow-up cystoscopy, another 50 ml of urine was obtained from every patient for analysis. The initial urine sample at first diagnosis was not available from one patient. All tumors were diagnosed according to the criteria of American Joint Committee on Cancer. Urine for cytology was prepared as described previously and cells were stained with standard Papanicolaou stain. The final diagnosis from cytopathology (at the Johns Hopkins Hospital) was entered in the study.

DNA extraction was performed as follows: Erythrocytes were lysed by subjecting the blood to TM-solution (5 mM MgCl, 20 mM Tris buffer), and samples were spun at 3000 r.p.m. for 10 min in order to obtain a leukocyte pellet. Urine was also spun at 3000 r.p.m. and the pellet was washed with phosphate-buffered saline. Tumor specimens were cut into 7-$\mu$m sections and standard hematoxylin and eosin staining was performed. After confirmation of the diagnosis, neoplastic tissue was microdissected. This material, as well as the leukocytes and the urine cell pellet, were digested with 1% SDS and 50 $\mu$g/ml proteinase K for 12 hr at 48° C. DNA was obtained from the samples by phenol-chloroform extraction and ethanol precipitation.

Microsatellite DNA analysis was performed as follows: DNA derived from leukocytes, urine and tumor was analyzed using a panel of twenty microsatellite DNA markers on different chromosomes (Research Genetics, Huntsville, Ala., and Oncor, Gaithersburg, Md.). This panel contained the thirteen markers used in our earlier study and seven new markers that revealed a high rate of loss of heterozygosity and shifts in primary bladder tumors.

Chromosomal location, sequences, and annealing temperatures (54–60° C.) of the seven new primer pairs are as follows:

```
for D8S3G7
(Chromosomal
arm 8p):

D8S3G7(F)
5'-GACCCTGTCAAGGAAAGAAAGAGA-3'
(SEQ ID
NO:53)

D8S3G7(R)
5'-CCATTTCAAATTTGGGACCACACTG-3'
(SEQ ID
NO:54)

for THO
(Chromosomal
arm 11q):

THO(F)
5'-AAGCTGCCCTAGTCAGCAC-3'
(SEQ ID
NO:55)

THO(R)
5'-GCTTCCGAGTGCAGGTCACA-3'
(SEQ ID
NO:56)

for D11S488
(Chromosomal
arm 11p):

D11S488(F)
5'-mGGAAGGAAGGAAGGAAAGG-3'
(SEQ ID
NO:57)

D11S488(R)
5'-CTGATAGCCTGACCTGACTGTG-3'
(SEQ ID
NO:58)

for D13S802
(Chromosomal
arm 13q):

D13S802(F)
5'-CACAGTGAGACTCTATCTCAAAAA-3'
(SEQ ID
NO:59)

D13S802(R)
5'-TCAGACTGGCTTAGACTGTGG-3'
(SEQ ID
NO:60)
```

-continued for D17S695
(Chromosomal
arm 17p):

D17S695(F)
5'-CTGGGCAACAAGAGCAAAATTC-3'
(SEQ ID
NO:61)

D17S695(R)
5'-mGTTGTTGTTCATTGACTTCAGTCT-3'
(SEQ ID
NO:62)

for D17S654
(Chromosomal
arm 17p):

D17S654(F)
5'-GACCTAGGCCATGTTCACAGCC-3'
(SEQ ID
NO:63)

D17S654(R)
5'-GACATCCATTGGCACCACCCCAA-3'
(SEQ ID
NO:64)

for D20S48
(Chromosomal
arm 20q):

D20S48(F)
5'-TCCAGTCCCATCTGGATTG-3'

D20S48(R)
5'-GAAATAAGTGATGCTGTGATG-3'

The new markers were chosen by empirically screening 50 bladder tumors with 85 tri- and tetra-nucleotide microsatellite DNA markers. Rates of loss of heterozygosity and shifts (new alleles) were assessed and the best markers were included into this study. Annealing temperatures, heterozygosity frequency, and length of polymerase chain reaction products from each loci were obtained from the Genome Data Base.

One primer of each marker pair was end-labeled with [$\gamma$-$^{32}$P] ATP (Amersham, Arlington Heights, Ill.) using T4-polynucleotide kinase (Gibco BRL, Gaithersburg, Md.). Genomic DNA (50 ng) was subjected to 35 polymerase chain reaction cycles at a denaturing temperature of 95° C. for 30 sec, followed by varying annealing temperatures ranging from 54–58° C. for 1 min, an extension step at 70° C. for 1 min and a final extension step at 70° C. for 5 min on Hybaid thermocyclers (Hybaid, Teddington, UK). Polymerase chain reaction products were then separated in denaturing 7% polyacrylamide-urea-formamide gels. The running distances were calculated according to the expected lengths of the polymerase chain reaction products. Autoradiography was performed overnight at −80° C. with Kodak X-OAAAT scientific imaging film (Eastman Kodak, Rochester, N.Y.). Loss of heterozygosity was scored in informative cases if a significant reduction (>30%) in the ratio of the signals from the urine and/or tumor alleles was observed in comparison with the corresponding normal (germline) alleles in the adjacent lane.

The results of this Example show the feasibility of the present invention. Loss of heterozygosity or mutations by microsatellite DNA analysis (a positive test) was found in the urine of eighteen (90%) of these patients. In each case, the genetic change in urine DNA was identical to that identified in the primary tumor. One of the two affected patients missed by microsatellite DNA analysis displayed no mutations at any of the twenty tested loci in the initial urine and tumor, but showed loss of heterozygosity at two loci (D16S476 and D9S162) in the follow-up urine sample collected five months preceding the eventual detection and resection of a recurrent tumor by cystoscopy. The other patient also showed no mutations in his initial urine or tumor sample with this set of markers. Although both of these patients had superficial, low grade tumors, similar tumors from other patients demonstrated multiple genetic changes on several chromosomal arms.

These patients were tested at routine cystoscopic evaluation at approximately four to six month intervals for up to twenty-six months. Recurrent tumors were observed in eleven of the twenty-one patients. Ten of these eleven patients (91%) were diagnosed correctly by microsatellite DNA analysis of the urine DNA collected at the time of follow-up visits. The urine samples of affected patients displayed multiple genetic changes on different chromosomal arms, confirming a "positive" result at several markers in many cases. These genetic changes were also identified in the DNA of paired tumor samples from each case when available. In two of these patients, a positive test preceded overt clinical diagnosis by cystoscopy.

The single false-negative result was from a patient who had a small pTa,GI recurrent tumor. Although urine samples and tumor biopsies exhibited multiple DNA changes at the initial presentation, the follow-up urine (and tumor) samples at five months appeared to be free of mutations at the screened loci.

Recurrence-free status was correctly identified at follow-up by microsatellite DNA analysis in ten of the ten patients (100%) who were disease-free after cystoscopy. In nine of these ten cases, genetic mutations present in urine at initial presentation reverted to normal on follow-up analysis. One elderly patient underwent a bladder-sparing treatment protocol for a T3 tumor. During multimodality treatment (chemotherapy and radiation therapy), the molecular test remained positive in the urine. At six month follow-up, the patient demonstrated no evidence of recurrent disease, and the molecular urine test reverted back to normal.

Cytologic analysis at the time of the last follow-up, also performed in a blinded fashion, was available from seventeen patients. Neoplastic cells were identified in only one of eight patients (13%) with recurrent lesions (two of the patients with recurrent disease were not evaluated by cytology). All nine patients without recurrent disease were correctly identified as negative by cytology (cytology was not performed in the two remaining cases).

In this Example, ten of eleven patients with recurrent transitional cell carcinoma of the urinary tract were identified by microsatellite DNA analysis of the urine collected at the time of routine follow-up. Even small tumors of low stage and grade exhibited multiple genetic mutations, allowing precise and definitive diagnosis. Most tumors were detected by loss of heterozygosity; however, one patient was detected by identification of "shifts" (new alleles) alone. The results of this Example support the theory that malignant cells can undergo enrichment by storage; tumor cells may be resistant to apoptosis and may survive longer than normal cells. Moreover, because the tumor surfaces contain rapidly growing cell populations, with mutations in cell-cell adhesion, malignant tumor cells are shed more readily and in greater numbers into the urine than normal cells.

The only patient (and the two patients at initial presentation) whose recurrent tumor could not be diagnosed from the urine had a small, low-grade lesion, without any microsatellite DNA abnormalities at the twenty tested markers. Thus, the molecular test did not miss any patients with genetic changes present at these markers in the primary tumors. This suggests that the lack of detection of loss of heterozygosity or shifts due to normal (non-tumor) cell contamination has not been a cause of false-negative results. Small Ta lesions show microsatellite DNA mutations as often as more invasive lesions, but they often harbor fewer regions of loss of heterozygosity. Theoretically, the use of a higher number of markers might further increase the sensitivity of the test.

Cytology detected one of eight patients with recurrent disease and missed six of seven patients with pTa lesions. Cytology usually detects approximately 50% of superficial lesions and in positive cases can help establish the diagnosis before cystoscopy. Failure to detect these small tumors may probably be less significant clinically. Progression to muscle-invasive tumors occurs in only 3% in this stage, and metastatic spread has been observed in 5% of patients. However, patients with these small lesions may also benefit from chemopreventive approaches to prevent progression, in addition to definitive resection. In this regard, molecular analysis appears more promising as a method for detecting these early lesions for additional interventions.

Ten of the ten patients without evidence of recurrent disease were diagnosed correctly by microsatelhte DNA analysis of the urine samples. Moreover, all examinations during clinically confirmed disease-free intervals also served as negative controls for each patient. Most patients with bladder cancer will develop recurrence within two years, and thus longer follow-up will be necessary in some patients to confirm the accuracy of molecular diagnosis.

Two patients were positive several months before clinical confirmation by cystoscopy. In these cases, the molecular changes obviously preceded the clinically overt macroscopic findings seen by cytoscopy. In another retrospective study in lung cancer, a positive molecular test in the sputum of one patient was found thirteen months before the development of lung cancer.

The status of recurrent disease was diagnosed correctly in a patient, from the follow-up urine sample with marker D17S695. It was intriguing that the recurrent tumor had three other distinct molecular mutations, yet none of these could be detected in the urine. This patient had multifocal disease. It is probable that the biopsy sample contained a clonal neoplastic population different from that identified in the urine. Biopsies from the other lesions were not available to definitely ascertain which tumor shed the predominant cell population into the urine.

The data in this Example provide an insight into the potential usefulness of microsatellite DNA urine analysis for monitoring patients for recurrent disease. This Example shows a high sensitivity for this assay in detecting recurrent tumors, demonstrating the first potential clinical utility for this approach. Moreover, the use of additional markers capable of identifying other areas of loss of heterozygosity may flirther improve the sensitivity of this test for bladder cancer. In addition to providing a positive or negative test, this assay may provide abundant molecular information regarding tumor progression and prognosis (see FIG. 5).

EXAMPLE 4

Analysis of Saliva in Cases of Head and Neck Cancer

One hundred and five incrosatellite DNA markers were screened in primary lung, and head and neck cancer, to find those most amenable to microsatellite DNA shifts. The eight best markers show the highest frequency of these shifts. These were tested in twenty-one paired samples of tumor and saliva in patients with head and neck cancer. The saliva samples were obtained by both swabbing and rinsing the mouth of the affected patients. In summary, fifteen out of the twenty-one cancer cases with just these eight markers were detected. In eight of these cases, a new allele or shift was identified in both a tumor and saliva, three patients in which there was both loss of heterozygosity and instability in the saliva and tumor, and four additional patients which showed only loss of heterozygosity in both the tumor and in the saliva with these markers. In addition, twenty-two control samples were tested of patients without cancer and found none of these mutations in saliva.

The invention now being fully described, it will be apparent to one of ordinary skill in the art that many changes and modifications can be made without departing from the spirit or scope of the invention.

I claim:

1. A method for detecting cancer or precancer in a subject, the method comprising:
   a) amplifying test sample DNA at a genetic locus for which the subject is heterozygous, wherein the genetic locus comprises a first and second alleles, said genetic locus comprising microsatellite DNA, wherein the test sample DNA is from a cell of an organ which drains into the test samples, wherein the test sample is selected from the group consisting of the subject's: urine, sputum, bile, stool, saliva, tears, serum and plasma; and
   b) detecting an allelic imbalance at the genetic locus by determining and comparing level of microsatellite DNA present at the first allele to level of microsatellite DNA present at the second allele, wherein an allelic imbalance is indicative of cancer or precancer.

2. The method of claim 1, wherein the allelic imbalance is a decrease in the level of microsatellite DNA present at the first allele.

3. The method of claim 2, wherein the level of microsatellite DNA present at the first allele in the test sample DNA is less than 50% of the level of microsatellite DNA present at the first allele in a control sample of the subject wherein the control sample lacks cancerous or precancerous cells.

4. The method of claim 1, wherein the allelic imbalance is an increase in the level of microsatellite DNA present at the first allele.

5. The method of claim 1, wherein the step of detecting comprises size fractionation of the first and second alleles.

6. The method of claim 5, wherein the first and second alleles are fractionated by gel electrophoresis.

7. The method of claim 1, wherein the subject has cancer.

8. The method of claim 7, wherein the cancer is selected from the group consisting of head, neck, lung, esophageal, stomach, small bowel, colon, bladder, kidney, and cervical cancer.

9. The method of claim 1, wherein said step of amplifying comprises a polymerase chain reaction.

10. The method of claim 1 wherein the genetic locus is selected from the group consisting of: DRPLA, UT762, IFNA, D9S200, D9S156, D3S1284, D3S1238, CHRNB1, D17S86, D9S747, D9S171, D16S476, D4S243, D14S50, D21S1245, FgA, D8S3G7, THOO, D115488, D135488, D135802, D175695, D175654, and D20548.

11. The method of claim 1, wherein said step of amplifying is performed using primers that hybridize to nucleotide sequences selected from the group consisting of SEQ ID NO:1–31 and SEQ ID NO:32.

12. The method of claim 11, wherein said primers are selected from the group consisting of SEQ ID NO:33–63 and SEQ ID NO:64.

13. The method of claim 1, wherein the cancer or precancer is not due to a DNA repair gene defect.

14. The method of claim 13, wherein the subject has cancer.

15. The method of claim 14, wherein the cancer is selected from the group consisting of the head, neck, lung, and bladder cancer.

16. The method of claim 14, wherein the subject has a benign neoplasm.

17. The method of claim 14, wherein the subject has a malignant neoplasm.

* * * * *

UNITED STATES PATENT AND TRADEMARK OFFICE
CERTIFICATE OF CORRECTION

PATENT NO.    : 6,291,163 B1                                          Page 1 of 1
DATED         : September 18, 2001
INVENTOR(S)   : David Sidransky It is certified that error appears in the above-identified patent and that said Letters Patent is hereby corrected as shown below:

Title page,
Item [56], References Cited, OTHER PUBLICATIONS, "Aaltonen, L., et al.," reference, "*Science*vol." has been replaced with -- *Science*, vol. --;

Column 51,
Line 31, "samples" has been replaced with -- sample --;

Column 52,
Lines 31-32, "D8S3G7, THOO, D115488, D135488, D135802, D175695, D175654, AND D20548." has been replaced with -- D8S307, THO1, D11S488, D13S488, D13S802, D175S695, D17S654, and D20S48. --

Signed and Sealed this

Eleventh Day of May, 2004

JON W. DUDAS
*Acting Director of the United States Patent and Trademark Office*